United States Patent [19]
Lohrmann

[11] Patent Number: 5,562,893
[45] Date of Patent: Oct. 8, 1996

[54] GAS-FILLED MICROSPHERES WITH FLUORINE-CONTAINING SHELLS

[75] Inventor: Rolf Lohrmann, La Jolla, Calif.

[73] Assignee: Molecular Biosystems, Inc., San Diego, Calif.

[21] Appl. No.: 284,782

[22] Filed: Aug. 2, 1994

[51] Int. Cl.$^6$ ................................................ A61K 49/00
[52] U.S. Cl. ........................................ 424/9.52; 424/9.5
[58] Field of Search ................................ 424/9.52, 9.51, 424/9.5; 252/312, 351

[56] References Cited

U.S. PATENT DOCUMENTS

| | | | |
|---|---|---|---|
| 4,957,656 | 9/1990 | Cerny et al. | 252/311 |
| 4,985,550 | 1/1991 | Charpiot et al. | 536/18.4 |
| 5,137,928 | 8/1992 | Erbel et al. | 521/56 |
| 5,149,543 | 9/1992 | Cohen et al. | 424/499 |
| 5,190,982 | 3/1993 | Erbel et al. | 521/56 |
| 5,234,680 | 8/1993 | Rogers, Jr. et al. | 424/9 |
| 5,409,688 | 4/1995 | Quay | 424/9.52 |
| 5,446,023 | 8/1995 | Pavia et al. | 514/12 |

FOREIGN PATENT DOCUMENTS

| | | |
|---|---|---|
| 0458745 | 11/1991 | European Pat. Off. . |
| 0554213 | 8/1993 | European Pat. Off. . |
| WO89/06978 | 8/1989 | WIPO . |
| WO91/09629 | 7/1991 | WIPO . |
| WO91/12823 | 9/1991 | WIPO . |
| WO92/05806 | 4/1992 | WIPO . |
| WO92/17212 | 10/1992 | WIPO . |
| WO92/17213 | 10/1992 | WIPO . |
| WO92/18164 | 10/1992 | WIPO . |
| WO93/02712 | 2/1993 | WIPO . |

OTHER PUBLICATIONS

Ophir et al., "Contrast agents in diagnostic ultrasound" *Ultrasound in Med. & Biol.* (1989) 15(4):319–333.
Schneider et al., "Polymeric microballons as ultrasound contrast agents. Physical and ultrasonic properties compared with sonicated albumin" *Invest. Radiol.* (1992) 27(2):134–139.
Zeifman et al., "The chemistry of perfluoroisobutene" *Russian Chem. Rev.* (1984) 53(3):256–273, translated from: *Uspekhi Khimii* (1984) 53:431–461.
Dyatkin et al., "The perfluoro-t-butyl anion in the synthesis of organofluorine compounds" *Russian Chem. Rev.* (1976) 45(7): 607–614, translated from: *Uspekhi Khimii* (1976) 45: 1205–1221.
Wen et al., "Thermodynamics of some perfluorocarbon gases in water" *J. Solution Chem.* (1979) 8(3): 225–246.
Knunyants, I. L., et al., eds., *Synthesis of Fluoroorganic Compounds*, (1985) Springer–Verlag, New York, pp. 1–299.
Olah, G. A., et al., eds., *Synthetic Fluorine Chemistry*, (1992) John Wiley & Sons, Inc., New York, pp. 227–245.
March, J., ed., *Advanced Organic Chemistry*, (1992) John Wiley & Sons, Inc., New York, pp. 417–418.

*Primary Examiner*—Richard L. Raymond
*Assistant Examiner*—Mary C. Cebulak
*Attorney, Agent, or Firm*—Morrison & Foerster

[57] ABSTRACT

Improved ultrasonic imaging contrast agents are provided which are comprised of an aqueous suspension of microspheres comprising at least one gas, preferably a perfluorocarbon, encapsulated by elastic shells of a biocompatible, fluorine-containing amphiphilic material, processes for making the microspheres, and methods of diagnostic imaging using the improved contrast agents.

19 Claims, No Drawings

GAS-FILLED MICROSPHERES WITH FLUORINE-CONTAINING SHELLS

DESCRIPTION

1. Technical Field

This invention is in the field of ultrasonic imaging. More particularly it relates to microspheres useful for ultrasonic imaging which comprise microbubbles of gas encapsulated by shells composed of a biocompatible, fluorine-containing amphiphilic material, aqueous suspensions of such microspheres and the use of such suspensions in ultrasonic imaging.

2. Background

Diagnostic ultrasonic imaging is based on the principle that waves of sound energy can be focused upon an area of interest and reflected in such a way as to produce an image thereof. The ultrasonic transducer is placed on a body surface overlying the area to be imaged, and ultrasonic energy in the form of sound waves is directed toward that area. As ultrasonic energy travels through the body, the velocity of the energy and acoustic properties of the body tissue and substances encountered by the energy determine the degree of absorption, scattering, transmission and reflection of the ultrasonic energy. The transducer then detects the amount and characteristics of the reflected ultrasonic energy and translates the data into images.

As ultrasound waves move through one substance to another there is some degree of reflection at the interface. The degree of reflection is related to the acoustic properties of the substances defining the interface. If these acoustic properties differ, such as with liquid-solid or liquid-gas interfaces, the degree of reflection is enhanced. For this reason, gas-containing contrast agents are particularly efficient at reflecting ultrasound waves. Thus, such contrast agents intensify the degree of reflectivity of substances encountered and enhance the definition of ultrasonic images.

Ophir and Parker describe two types of gas-containing imaging agents: (1) free gas bubbles; and (2) encapsulated gas bubbles (*Ultrasound in Medicine and Biology* 15(4):319–333 (1989)), the latter having been developed in an attempt to overcome instability and toxicity problems encountered using the former. Encapsulated gas bubbles, hereinafter referred to as "microspheres", are composed of a microbubble of gas surrounded by a shell of protein or other biocompatible material. One such imaging agent is ALBUNEX® (Molecular Biosystems, Inc., San Diego, Calif.) which consists of a suspension of air-filled albumin microspheres.

Generally, microspheres of a particular gas exhibit improved in vivo stability when compared to free bubbles of the same gas. However, most microspheres still have relatively short in vivo half lives which compromise their usefulness as contrast agents. This instability in vivo was thought to result from the collapse or breakdown of the shells under pressure resulting in rapid diffusion of the gas from the microspheres. Thus, many recent efforts have centered on improvements to the shell as a way of increasing in vivo stability. Known improvements relating to protein-shelled microspheres include coating the protein shell with surfactants (Giddy, WO 92/05806) and chemical cross-linking of the protein shell (Holmes et al., WO92/17213).

Additional efforts directed toward improving microsphere stability include the use of non-proteinaceous shell-forming materials. Bichon et al. (EPA 458,745 A1) and Schneider et al. (*Inv. Radiol.* 27:134–139 (1992)) describe the production of polymeric "microballoons" made of interfacially deposited polymers encapsulating various gases such as carbon dioxide, nitrous oxide, methane, freon, helium and other rare gases. Klaveness (WO92/17212) describe the use of chemically-linked, non-proteinaceous amphiphilic moieties encapsulating "air, nitrogen, oxygen, hydrogen, nitrous oxide, carbon dioxide, helium, argon, sulfur hexafluoride and low molecular weight, optionally fluorinated, hydrocarbons such as methane, acetylene or carbon tetrafluoride." Erbel et al. (U.S. Pat. No. 5,190,982) describe the use of polyamino-dicarboxylic acid-co-imide derivatives.

More recently, Schneider, et al. (European Patent Application 554,213 A1) have demonstrated that microspheres containing gases with certain physical properties have improved stability. It is theorized that microsphere instability is caused by the increase in pressure to which microspheres are exposed once they are introduced into the circulatory system. Although Schneider, et al. do not speculate as to the mechanism responsible for their observed enhanced pressure resistance, we believe it is due to the effects of gas solubility on the rate of gas exchange with the aqueous environment.

According to the principles of Henry's law, as pressure increases, the solubility of a given gas in solution will also increase. When a bubble of gas in solution is subjected to pressure, the rate of gas exchange between the gas in the bubble and the surrounding solution will increase in proportion to the amount of pressure, and the bubble of gas will eventually become completely solubilized. The more insoluble the gas is in the surrounding solution, the longer it will take for a bubble to become completely solubilized.

If the bubble of gas is surrounded by a shell, i.e in the form of a microsphere, the effects of gas exchange are still observed, since microsphere shells do not completely eliminate the contact between the gas in the microsphere and the surrounding solution. Hence, when microspheres suspended in solution are subjected to pressure, the gas inside the microspheres eventually becomes solubilized in the surrounding solution which results in collapse of the microspheres.

Microspheres useful for ultrasonic imaging typically have shells with a certain degree of elasticity. This property is necessary for two important reasons. Firstly, microspheres having shells which are rigid may resonate at frequencies higher than those used for ultrasonic imaging which lessens their efficiency as contrast enhancers. Secondly, rigid-shelled microspheres can crack or break when subjected to pressure thus releasing their gaseous contents into the aqueous environment. Elastic-shelled microspheres while able to overcome the aforementioned problems may unfortunately be more susceptible to the effects of gas exchange with the aqueous environment because of their tendency to be more permeable. This results in a greater degree of contact between the gas inside the microsphere and the surrounding aqueous environment thus facilitating gas exchange.

In order to inhibit the exchange of gas in the microsphere center with the surrounding aqueous environment, the present invention describes the introduction of fluorine into the microsphere shell material. Microspheres having fluorine-containing shells will exhibit decreased water permeability and thus enhanced resistance to pressure instability due to gas exchange.

DISCLOSURE OF THE INVENTION

The present invention provides compositions and methods of ultrasonic imaging using novel gas-filled microspheres that have fluorine-containing shells. In particular, the present invention provides compositions for use as ultrasonic imaging agents comprising aqueous suspension of microspheres, the microspheres comprising a fluorine-containing shell formed from amphiphilic, biocompatible material surrounding a microbubble of at least one biocompatible gas.

The gas is preferably insoluble and is more preferably fluorinated and even more preferably a $C_1$ to $C_5$ perfluorocarbon. Suitable perfluorinated gases include perfluoromethane, perfluoroethane, perfluoropropane, perfluorobutane and perfluoropentane.

Suitable fluorine-containing shell material includes lipids, proteins (which includes both naturally occurring proteins and synthetic amino acid polymers), synthetic organic polymers and mixtures and copolymers thereof. The shell material is preferably a protein, and more preferably human serum albumin.

The present invention also provides a process for making microspheres with fluorine-containing shells which involves reacting the shell material with a fluorine-containing reactive compound which effects the introduction of fluorine moieties into the shell material.

The present invention further provides a method to enhance the contrast of tissues and organs in an ultrasonic image comprising the steps of injecting the above described composition into a subject and detecting an ultrasonic image.

MODES OF CARRYING OUT THE INVENTION

The present invention relates to stabilized microspheres which comprise a fluorine-containing shell formed from biocompatible material surrounding a microbubble of gas. Such shell material is less water permeable than its non-fluorine-containing equivalent. In addition, interactions which take place between certain gases and the shell may further stabilize the microsphere. In particular, when the gas also contains fluorine, the fluorine-fluorine interactions between the gas and shell provide an additional barrier to gas exchange with the surrounding aqueous environment.

Suitable shell material must be amphiphilic, i.e., containing both hydrophobic and hydrophilic moieties. It must also be capable of forming a thin layer or skin around the encapsulated gas, which will generally result in hydrophilic groups oriented externally and hydrophobic groups oriented internally. When microspheres are produced to contain insoluble gas, this orientation is believed to be enhanced by the presence of the insoluble gas during microsphere formation.

The shell thus formed must also be solid. The term solid is used to refer to the state of matter at the temperature of a subject being imaged which is distinguished from either the liquid or gaseous state, and is characterized generally as being discrete, non-fluid and capable of maintaining form or shape. Compositions which are quasi-liquid at the temperature at which the subject is imaged (the imaging temperature), such as certain lipids having transition temperatures close (i.e. within 15° C.) to imaging (body) temperature have some of the characteristics of both liquids and solids. These quasi-liquids are also contemplated by the present invention and included in the term solid. The thickness of a microsphere shell will depend primarily on its rigidity when formed but will generally be in the range of 10 to 500 nm.

Different classes of materials that would be suitable for forming microsphere shells include, but are not limited to, lipids, proteins (both naturally occurring and synthetic amino acid polymers), synthetic organic polymers, and mixtures or copolymers thereof. Lipid shells can be formed from either naturally occurring or synthetic lipids, for example, phospholipids, such as phosphoglycerides, phosphatidic acid, phosphatidylcholine, phosphatidyl serine, phosphatidylethanolamine, phosphatidyl inositol, phosphatidylglycerol, diphosphatidyl-glycerol (cardiolipin); glycolipids, such as cerebrosides, galactocerebrosides, glucocerebrosides, sphingomyelin, sphingolipids, derivatized with mono-, di- and trihexosides, sulfatides, glycosphingolipid, and lysophosphatidylcholine; unsaturated fatty acids, such as palmitoleic acid, oleic aid, vaccenic acid, linoleic acid, α-linolenic acid and arachidonic acid; saturated fatty acids, such as myristic acid, palmitic acid, stearic acid, arachidic acid, behenic acid, lignoceric acid and cerotic acid; mono-, di- and triglycerides; and steroids, such as cholesterol, cholesterol esters, cholestanol, ergosterol, coprostanol, squalene, and lanosterol.

Shells consisting predominantly of lipids will generally be oriented with the hydrophobic side adjacent the gas while the hydrophilic side forms the external microsphere surface. The hydrophilic moieties of most lipids are polar, i.e., cationic or anionic such as the phosphate moiety of a phospholipid, or they can be zwitterionic as in phosphatidyl cholines. Alternatively, lipids without polar groups can be made polar such as by introduction of non-ionic hydrophilic moieties, for example polyethylene glycol, or carbohydrates.

Phospholipids are a particularly useful sub-class of lipid shell materials. The various phospholipids have characteristic phase transition temperatures, Tc, below which the fatty acyl chains form a quasi-crystalline structure and above which the chains are in a more quasi-liquid state. Their ability to transition from quasi-crystalline to quasi-liquid with increases in temperature can facilitate the production of microspheres that become more elastic in-vivo. For example, using a phospholipid with a Tc which is between 25° C. and 37° C., a solid shelled microsphere can be formed at room temperature (20°–25° C.) which becomes less rigid at an imaging temperature of 37° C. This may lead to enhanced echogenicity due to improved shell elasticity. Phospholipids having lower Tc values, for example, dimyristoyl or dipentadecanoyl glycerophosphocholine, are particularly suitable for use in this aspect of the invention.

A comparison of the Tc values of a series of synthetic L-α-lecithins (1,2-diacyl-sn glycero-3-phosphocholines, or glycerophosphocholines) reveals that Tc increases steadily relative to hydrocarbon chain length. Dipalmitoyl glycerophosphocholine has a Tc of 41° C., while the dimyristoyl derivative has a Tc of 23° C. The distearoyl and diarachidoyl derivatives have Tcs of 55° C. and 66° C., respectively. It is also contemplated that a mixture of these and other phospholipids that have different Tc values could also be used to achieve the desired transitional characteristics of the microsphere shells. Further, the gas in the microsphere and the introduction of fluorine into the shell material may alter the Tc value. This effect should be considered when selecting the phospholipid.

Lipid shells may also optionally incorporate proteins, amino acid polymers, carbohydrates or other substances useful for altering the rigidity, elasticity, biodegradability and/or biodistribution characteristics of the shell. Incorporation of sterols is particularly useful in increasing the rigidity of the shell. The rigidity of the shell can also be enhanced by cross-linking, for example, with irradiation.

Protein shell material includes both naturally-occurring proteins and synthetic amino acid polymers which herein are both generally referred to as being in the class of shell materials described as "proteins". Examples of naturally-occurring proteins include gamma-globulin (human), apo-transferrin (human), beta-lactoglobulin, urease, lysozyme, and albumin. Synthetic amino acid polymers can optionally be in the form of block or random co-polymers combining both hydrophobic and hydrophilic amino acids in the same or different chains.

The structure of a protein or an amino acid polymer is represented as:

$$H_3\overset{\oplus}{N}-\underset{R}{CH}-\overset{O}{\overset{\|}{C}}-(NH-\underset{R}{CH}-C)_n-NH-\underset{R}{CH}-COO^{\ominus}$$

wherein R is the side chain of the amino acid (for example, the R of cysteine is $HSCH_2$) The amino acid side chain will also generally be the fluorine-containing portion of the protein/polymer.

Synthetic organic polymers are also suitable for forming microsphere shells. These polymers can consist of a single repeating unit or different repeating units which form a random, alternating or block-type co-polymer. These organic polymers include cross-linked polyelectrolytes such as phosphazenes, imino-substituted polyphosphazenes, polyacrylic acids, polymethacrylic acids, polyvinyl acetates, polyvinyl amines, polyvinyl pyridine, polyvinyl imidazole, and ionic salts thereof. Cross-linking of these polyelectrolytes is accomplished by reaction with multivalent ions of the opposite charge. Further stabilization can be accomplished by adding a polymer of the same charge as the polyelectrolyte. See U.S. Pat. No. 5,149,543 which is incorporated herein by reference.

Additional synthetic organic monomeric repeating units which can be used to form polymers suitable for shell materials within the present invention are hydroxyacids, lactones, lactides, glycolides, acryl containing compounds, aminotriazol, orthoesters, anhydrides, ester imides, imides, acetals, urethanes, vinyl alcohols, enolketones, and organosiloxanes.

The introduction of fluorine into the shell material can be accomplished by any known method. For example, the introduction of perfluoro-t-butyl moieties is described in U.S. Pat. No. 5,234,680; SYNTHESIS OF FLUOROORGANIC COMPOUNDS (Springer-Verlag, New York, 1985); Zeifman, Y. V. et al., Uspekhi Khimii (1984) 53 p. 431; and Dyatkin, B. L. et al., Uspekhi Khimii (1976) 45, p. 1205. These methods generally involve the reaction of perfluoroalkyl carbanions with host molecules as follows:

$$(CF_3)_3C^-+R-X>(CF_3)_3C-R$$

where R is a host molecule and X is a good leaving group, such as Br, Cl, I or a sulfonato group. After adding a leaving group to the foregoing monomeric shell materials using methods well known in the art, perfluoro-t-butyl moieties can then be easily introduced to these derivatized shell materials (the host molecules) in the manner described above.

Additional methods are known for the introduction of trifluoromethyl groups into various organic compounds. One such method describes the introduction of trifluoromethyl groups by nucleophilic perfluoroalkylation using perfluoroalkyl-trialkylsilanes. (SYNTHETIC FLUORINE CHEMISTRY pp. 227–245 (John Wiley & Sons, Inc., New York, 1992)).

Fluorine can be introduced into any of the aforementioned shell materials either in their monomeric or polymeric form. Preferably, fluorine moieties are introduced into monomers, such as fatty acids, amino acids or polymerizable synthetic organic compounds, which are then polymerized for subsequent use as microsphere shell-forming material.

The introduction of fluorine into the shell material may also be accomplished by forming microspheres in the presence of a perfluorocarbon gas. For example, when microspheres are formed from proteins such as human serum albumin in the presence of a perfluorocarbon gas, such as perfluoropropane, using mechanical cavitation, fluorine from the gas phase becomes bound to the protein shell during formation. The presence of fluorine in the shell material can be later detected by NMR of shell debris which has been purified from disrupted microspheres. Fluorine can also be introduced into microsphere shell material using other methods for forming microspheres, such as sonication, spray-drying or emulsification techniques.

Another way in which fluorine can be introduced into the shell material is by using a fluorine-containing reactive compound. The term "reactive compound" refers to compounds which are capable of interacting with the shell material in such a manner that fluorine moieties become covalently attached to the shell material. When the shell forming material is a protein, preferred reactive compounds are either alkyl esters or acyl halides which are capable of reacting with the protein's amino groups to form an amide linkage via an acylation reaction (see ADVANCED ORGANIC CHEMISTRY pp. 417–418 (John Wiley & Sons, New York, N.Y., 4th ed., 1992)). The reactive compound can be introduced at any stage during microsphere formation, but is preferably added to the gas phase prior to microsphere formation. For example, when microspheres are to be made using mechanical or ultrasound cavitation techniques, the reactive compound can be added to the gas phase by bubbling the gas to be used in the formation of the microspheres (starting gas) through a solution of the reactive compound. This solution is kept at a constant temperature which is sufficient to introduce a desired amount of reactive compound into the gas phase. The resultant gas mixture, which now contains the starting gas and the reactive compound, is then used to form microspheres. The microspheres are preferably formed by sonication of human serum albumin in the presence of the gas mixture as described in U.S. Pat. No. 4,957,656, which is incorporated herein by reference.

Suitable fluorine-containing alkyl esters and acyl halides are provided in Table I:

TABLE I

| REACTIVE COMPOUND | BOILING POINT* (°C.) |
|---|---|
| ALKYL ESTERS: | |
| diethyl hexafluoroglutarate | 75 (at 3 mm Hg) |
| diethyl tetrafluorosuccinate | 78 (at 5 mm Hg) |
| methyl heptafluorobutyrate | 95 |
| ethyl heptafluorobutyrate | 80 |
| ethyl pentafluoropropionate | 76 |
| methyl pentafluoropropionate | 60 |
| ethyl perfluorooctanoate | 167 |
| methyl perfluorooctanoate | 159 |
| ACYL HALIDES: | |
| nonafluoropentanoyl chloride | 70 |
| perfluoropropionyl chloride | 8 |
| hexafluoroglutaryl chloride | 111 |
| heptafluorobutyryl chloride | 38 |

*at 1 atm (760 mm Hg) unless otherwise noted above

In addition to the use of alkyl esters and acid halides described above, it is well known to those skilled in synthetic organic chemistry that many other fluorine-containing reactive compounds can be synthesized, such as aldehydes, isocyanates, isothiocyanates, epoxides, sulfonyl halides, anhydrides, acid halides and alkyl sulfonates, which contain perfluorocarbon moieties (—$CF_3$, —$C_2F_5$, —$C_3F_4$, —$C(CF_3)_3$). These reactive compounds can then be used to introduce fluorine moieties into any of the aforementioned shell materials by choosing a combination which is appropriate to achieve covalent attachment of the fluorine moiety.

Sufficient fluorine should be introduced to decrease the permeability of the microsphere shell to the aqueous environment. This will result in a slower rate of gas exchange with the aqueous environment which is evidenced by enhanced pressure resistance. Although the specific amount of fluorine necessary to stabilize the microsphere will depend on the shell material and the gas contained therein, after introduction of fluorine the shell material will preferably contain 0.5 to 20 percent by weight, and more preferably 1 to 10 percent by weight.

Gases suitable for use within the present invention are pharmacologically acceptable, i.e., biocompatible and minimally toxic to humans. The term "biocompatible" means the ability of the gas to be metabolized without the formation of toxic by-products. The term "gas" refers to any compound which is a gas or capable of forming gas at the temperature at which imaging is being performed (typically normal physiological temperature). The gas may be composed of a single compound or a mixture of compounds. Examples of gases suitable for use within the present invention are air, $O_2$, $N_2$, $H_2$, $CO_2$, $N_2O$; noble gases such as argon, helium, xenon; hydrocarbon gases such as methane, ethane, propane, n-butane, isobutane and pentane, and perfluorocarbon gases such as perfluoromethane, perfluoroethane, perfluoropropane, perfluorobutane, perfluoroisobutane and perfluoropentane. The gas is preferably a perfluorocarbon which is insoluble in water, which intends a solubility of less than 0.01 mL of gas per mL of water at atmospheric pressure and a temperature of 25° C. This degree of insolubility results in maximum stability in vitro and persistence in vivo. Solubility can be determined by any appropriate method. See, for example, Wen-Yang Wen et al. (1979) *J. Solubility Chem.* 8(3):225–246. A non-exhaustive list of preferred insoluble gases suitable for use within the present invention is provided in Table II.

different from those of blood or tissue. The maximum size (mean diameter) of the microsphere is defined by that size which will pass through the pulmonary capillaries. In the case of humans, that size will typically be less than about 10 micrometers. Correspondingly, the minimum size is that which will provide efficient acoustic scattering at the ultrasonic frequencies typically used for ultrasonic imaging. (The frequency may vary with the mode of imaging, e.g., transthoracic, transesophageal, and will normally be in the range of 2–12 MHz.) The minimum size will typically be about 0.1 micrometers. The typical mean size of the microspheres used in the invention method will be about 2 to about 7 micrometers. This size will permit their passage through capillaries, if necessary, without being filtered out prior to reaching the area to be imaged (e.g., where a peripheral venous injection site is used). Thus, microspheres within the present invention will be capable of perfusing tissue and producing an enhanced image of the tissue, organs and any differentiation between well-perfused and poorly-perfused tissue, without being injected into the arteries or directly into the area to be imaged. Accordingly, they may be injected into a peripheral vein or other predetermined area of the body, resulting in considerably less invasion than the arterial injections required for an angiogram.

Microspheres within the present invention may be used for imaging a wide variety of areas. These areas include, but are not limited to, myocardial tissue, liver, spleen, kidney, and other tissues and organs presently imaged by ultrasonic techniques. Use of microspheres within the present invention may result in an enhancement of such currently obtainable images.

Suspensions of microspheres are made by diluting the microspheres after formation to the desired concentration preferably $5\times10^7$ to $5\times10^9$ microspheres per mL, of suspending liquid which can be any aqueous, biologically-compatible liquid. Examples of such liquids are buffers, saline, protein solutions and sugar solutions.

A microsphere suspension within the present invention is stable both in vivo and in vitro. Stability in vivo is a function of the ability of a concentrated suspension (approximately $1\times10^9$ microspheres per mL) to withstand 40 pounds per

TABLE II

| FORMULA | NAME | MOLECULAR WEIGHT (g/mol) | BOILING POINT (°C.) | WATER SOLUBILITY at 25° C. and 1 atm (mL/mL × $10^{-3}$) |
|---|---|---|---|---|
| $SF_6$ | sulfur hexafluoride | 146 | −64 | 5.40 |
| $CF_4$ | perfluoromethane | 88 | −130 | 5.04 |
| $C_2F_6$ | perfluoroethane | 138 | −78 | 1.38 |
| $CF_3CF_2CF_3$ | perfluoropropane | 188 | −37 | <1 |
| $CF_3(CF_2)_2CF_3$ | perfluorobutane | 238 | −2 | <1 |
| $CF_3(CF_2)_3CF_3$ | perfluoropentane | 288 | 29.5 | <1 |

The microspheres of the present invention may be made by known methods used to make conventional gas-filled microspheres such as sonication, mechanical cavitation using a milling apparatus, or emulsion techniques. Such techniques are exemplified in U.S. Pat. Nos. 4,957,656; 5,137,928; 5,190,982; 5,149,543: PCT Application Nos. WO 92/17212; WO 92/18164; WO 91/09629; WO 89/06978; WO 92/17213; GB 91/12823; and WO 93/02712: and EPA Nos. 458,745 and 534,213 which are incorporated herein by reference.

The microspheres of the present invention are echogenic (i.e., capable of reflecting sound waves) being composed of material having acoustic properties which are significantly square inch (psi) pressure as evidenced by no appreciable change in size distribution after one minute at this pressure.

In terms of method of operation, the use of the subject microspheres would be the same as that of conventional ultrasonic contrast agents. The amount of microspheres used would be dependent on a number of factors including the choice of liquid carriers (water, sugar solution, etc.), degree of opacity desired, areas of the body to be imaged, site of injection and number of injections. In all instances, however, sufficient microspheres would be used in the liquid carrier to achieve enhancement of discernable images by the use of ultrasonic scanning.

The invention is further illustrated by the following examples. These examples are not intended to limit the invention in any manner.

EXAMPLE 1

Preparation of Microsphere Consisting of a Lipid-Based Material Encapsulating an Insoluble Gas A phosphatidyl choline is fluorinated as follows: A ω-bromo carboxylic acid ester $(Br(CH_2)_nCOOCH_2CH_3)$ and perfluorisobutylene $((CF_3)_2CF=CF_2)$ are reacted in the presence of CsF and monoglyme at room temperature to form a fluorinated ester $((CF_3)_3C(CH_2)_nCOOCH_2CH_3)$. This ester is hydrolyzed to form a free acid $((CF_3)_3C(CH_2)_nCOOH)$ which is converted to the acylchloride $((CF_3)_3C(CH_2)_nCOCl)$ by reacting it with thionyl chloride. The acylchloride is reacted in the presence of base with glycerophosphocholine to form the fluorinated glycerophosphocholine as follows:

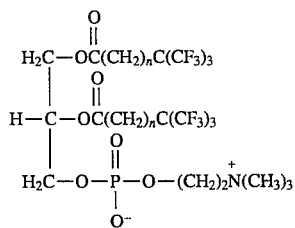

The length of the carbon chain of the bromo carboxylic acid ester used can be varied, for example between C5 and C20.

Microspheres are formed by first emulsifying the following ingredients to form an oil-in-water emulsion: fluorinated glycerophosphocholine (either alone or in combination with other lecithins), an insoluble gas (for example, see Table II above) and water. Optionally, the emulsion contains triolein, cholesterol and/or α-tocopherol. Homogenization of the emulsion is carried out under pressure and at a temperature above the transition temperature of the fluorinated glycerophosphocholine, followed by cooling to room temperature.

EXAMPLE 2

Preparation of a Synthetic Amino Acid Polymer Containing Fluorine Using a Polymer as the Starting Material A polyglutamic acid polymer containing fluorine (poly-sodium L-glutamate-co-perfluoro-t-butyl propylglutamine) was prepared as follows: Poly L-glutamic acid (m.w. 95,000, 1.77 g, 13.7 mmol) was dissolved in 40 mL of dimethylformamide (DMF) at 50° C. After cooling to room temperature, 10 mL pyridine, 1-hydroxybenzotriazole (1.85 g, 13.7 mmol) and perfluoro-t-butyl-propylamine hydrochloride (2.15 g, 6.85 mmol) were added. The reaction mixture was rendered anhydrous by evaporation of pyridine in vacuo. Dicyclohexylcarbodiimide (2.82 g, 13.7 mmol) was added and the solution stirred at room temperature for 48 hours. N,N'-dicyclohexylurea was removed by filtration and the filtrate poured into water adjusted to pH 3.0. The precipitate formed was filtered off and subsequently dissolved in water at pH 8.0. Undissolved material was removed by filtration (0.22μ membrane filter). The polymer solution was dialyzed overnight to remove soluble low-molecular weight material. The polymer solution was lyophilized yielding a white sponge-like material consisting of poly sodium L-glutamate-co-perfluoro-t-butyl propylglutamine.

The resultant fluorinated polyglutamic acid has the structure:

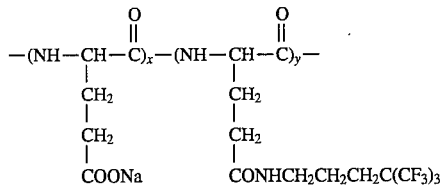

with the fluorinated moieties being present randomly in approximately 40–50% of the glutamic acid residues in the polymer.

The polymer is then added to human serum albumin, for example in a ratio of 1:10, and microspheres are produced as described in Examples 4 or 5.

EXAMPLE 3

Preparation of a Synthetic Amino Acid Polymer Containing Fluorine Using a Monomer as the Starting Material A poly-amino acid polymer containing fluorine (poly-3-(perfluoro-t-butyl)-2-aminobutyric acid) is synthesized as follows:

Bromoacetaldehyde diethyl acetal is reacted with perfluoroisobutylene in the presence of CsF and diglyme to yield:

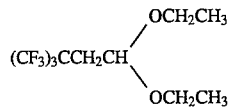

Acid hydrolysis of the diethyl acetal gives the aldehyde. Strecker synthesis with ammonium cyanide yields the corresponding amino nitrile:

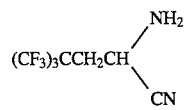

Hydrolysis gives the following amino acid derivative:

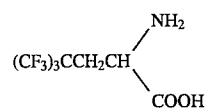

This compound is polymerized either alone or with other amino acids using known methods to form a fluorine-containing synthetic amino acid polymer.

The polymer is then added to human serum albumin, for example in a ratio of 1:10, and microspheres are produced as described in Examples 4 or 5.

EXAMPLE 4

Method of Making Microspheres by Mechanical Cavitation

Microspheres are produced using the shell-forming materials of Example 2 or 3 as follows: A 5% solution is deaerated under continuous vacuum for two hours. The vacuum is released by filling the evacuated vessel with the gas to be used for formation of the microspheres. The solution is adjusted to a temperature (about 68° C.) necessary to achieve local denaturation of the albumin upon cavitation via an in line heat exchanger and pumped at about 100 mL/min into a colloid mill, for example, a 2" colloid mill (Greerco, Hudson N.H., model W250V or AF Gaulin, Everett, Mass., model 2F). The gas, at room temperature, is added to the liquid feed just upstream of the inlet port at a flow rate of about 120–220 mL/min. The gap between the rotor and the stator is adjusted to about 2/1000th inch and the albumin solution is milled continuously at about 7000 rpm at a process temperature of about 73° C.

The dense white solution of microspheres thus formed is immediately chilled to a temperature of about 10° C. by a heat exchanger, and collected in glass vials. The vials are immediately sealed.

EXAMPLE 5

Method of Making Microspheres by Sonic Cavitation

Microspheres are produced using the shell-forming materials of Example 2 or 3 as follows: A 5% solution is deaerated under continuous vacuum for two hours. The vacuum is released by filling the evacuated vessel with the gas to be used for formation of the microspheres. The continuous sonication process is performed as described by Cerny (U.S. Pat. No. 4,957,656).

The dense white solution of microspheres thus formed is immediately chilled to a temperature of about 10° C. by a heat exchanger, and collected in glass vials. The vials are immediately sealed.

EXAMPLE 6

Pressure Resistance of Microspheres

Microspheres with fluorine-containing shells are prepared as described in Examples 4 or 5 above. A ten mL aliquot of each suspension adjusted to a concentration of approximately $1\times10^9$ microspheres per mL in phosphate buffered saline is placed in a 10 mL glass gas-tight syringe (Hamilton, Reno Nev.) fitted with a pressure gauge. All headspace is removed and the apparatus is sealed. A constant pressure of about 40 psi is applied for about 3 minutes. A Coulter Counter is used to measure the sample particle concentration and distribution. Stable microspheres exhibit no significant change (less than 10%) in the mean size of the microspheres after application of pressure.

EXAMPLE 7

Elasticity

Microspheres with fluorine-containing shells are prepared as described in Examples 4 or 5 above. Microspheres are diluted into phosphate buffered saline to a concentration of approximately $1\times10^9$ microspheres per mL and placed in a clear cell positioned on the stage of a microscope. The cell is connected to a nitrogen source that allows observation of the effects of rapid application and release of up to 3 psi pressure on the microspheres. Elastic microspheres are capable of returning to their original dimensions after release of applied pressure.

EXAMPLE 8

Diagnostic Imaging

Microspheres prepared as described in Examples 4 and 5 are used in diagnostic imaging as follows: For a dog weighing approximately 25 Kg, a 1.0 mL volume of a microsphere suspension containing $5\times10^7$ to $5\times10^9$ microspheres per mL is injected into a peripheral (cephalic) vein at a rate of 0.3 mL per second. Images of the heart are acquired using a Hewlett Packard Sonos 1500 (Andover, Mass.) ultrasonograph in the B-mode using a transthoracic 5.0 mHz transducer. Images are recorded at a frame rate of 30 frames per second throughout the procedure and stored on S-VHS tape for later processing.

What is claimed is:

1. A composition for use as an ultrasonic imaging agent comprising an aqueous suspension of microspheres, said microspheres comprising a shell of fluorine-containing amphiphilic, biocompatible material surrounding a microbubble of at least one biocompatible gas.

2. The composition of claim 1, wherein the gas has a solubility of less than 0.01 mL per mL of water at 25° C. and 1 atm.

3. The composition of claim 2, wherein the gas is a perfluorocarbon.

4. The composition of claim 3, wherein the perfluorocarbon gas is selected from the group consisting of perfluoromethane, perfluoroethane, perfluoropropane, perfluorobutane and perfluoropentane.

5. The composition of claim 1, wherein the gas is a hydrocarbon.

6. The composition of claim 5, wherein the hydrocarbon gas is selected from the group consisting of methane, ethane, propane, n-butane, isobutane and pentane.

7. The composition of claim 1, wherein the shell comprises a fluorine-containing amphiphilic, biocompatible material selected from the group consisting of lipids, proteins, and synthetic organic polymers.

8. The composition of claim 1, wherein the fluorine-containing amphiphilic biocompatible material is a lipid.

9. The composition of claim 8, wherein the lipid is a phospholipid.

10. The composition of claim 1, wherein the fluorine-containing amphiphilic biocompatible material is a protein.

11. The composition of claim 10 wherein the protein is human serum albumin.

12. The composition of claim 1, wherein the fluorine-containing amphiphilic biocompatible material is a synthetic organic polymer.

13. The composition of claim 1 wherein the microsphere shells contain 0.5 to 20 percent by weight fluorine.

14. A process for making pressure resistant microspheres, said microspheres comprising a shell of fluorine-containing amphiphilic, biocompatible material surrounding a microbubble of at least one biocompatible gas, said process comprising the steps of:

(a) introducing fluorine into an amphiphilic, biocompatible material by reacting a fluorine-containing reactive compound with said amphiphilic, biocompatible material to form a fluorine-containing amphiphilic, biocompatible shell material; and (b) simultaneously or subsequently forming said microspheres from said fluorine-containing amphiphilic, biocompatible shell material and said biocompatible gas.

15. The process of claim 14 wherein the reactive compound is selected from the group consisting of aldehydes, isocyanates, isothiocyanates, epoxides, alkyl esters, acyl halides, sulfonyl halides, anhydrides, acid halides, and alkyl sulfonates.

16. The process of claim 14 wherein the reactive compound contains at least one perfluorocarbon moiety selected from the group consisting of $-CF_3$, $-C_2F_5$, $-C_3F_7$ and $-C(CF_3)_3$.

17. The process of claim 14, further comprising forming the microspheres in the presence of at least one gas having a solubility of less than 0.01 mL per mL of water at 25° C. and 1 atm.

18. The process of claim 17 wherein the gas is a perfluorocarbon gas.

19. A method to enhance the contrast of tissues and organs of a patient in an ultrasonic image comprising:

(a) injecting the composition of claim 1 into the patient; and (b) ultrasonically imaging the tissues and organs while the composition is present therein.

* * * * *